US011111196B2

(12) United States Patent
Nakanishi et al.

(10) Patent No.: US 11,111,196 B2
(45) Date of Patent: Sep. 7, 2021

(54) 1,2-DICHLORO-1-(2,2,2-TRIFLUOROETHOXY)ETHYLENE, PRODUCTION METHOD THEREFOR, AND USES THEREOF

(71) Applicant: KANTO DENKA KOGYO CO., LTD., Tokyo (JP)

(72) Inventors: Akiko Nakanishi, Kurashiki (JP); Yutaka Nakamura, Shibukawa (JP)

(73) Assignee: KANTO DENKA KOGYO CO., LTD., Tokyo (JP)

( * ) Notice: Subject to any disclaimer, the term of this patent is extended or adjusted under 35 U.S.C. 154(b) by 0 days.

(21) Appl. No.: 16/761,702

(22) PCT Filed: Nov. 8, 2018

(86) PCT No.: PCT/JP2018/041420
§ 371 (c)(1),
(2) Date: May 5, 2020

(87) PCT Pub. No.: WO2019/093401
PCT Pub. Date: May 16, 2019

(65) Prior Publication Data
US 2021/0179977 A1 Jun. 17, 2021

(30) Foreign Application Priority Data
Nov. 9, 2017 (JP) .............................. JP2017-216532

(51) Int. Cl.
| C07C 43/17 | (2006.01) |
| C11D 7/32 | (2006.01) |
| C07C 41/06 | (2006.01) |
| C11D 7/28 | (2006.01) |
| C07C 41/09 | (2006.01) |
| C08J 9/14 | (2006.01) |

(52) U.S. Cl.
CPC .............. *C07C 43/17* (2013.01); *C07C 41/06* (2013.01); *C07C 41/09* (2013.01); *C11D 7/28* (2013.01); *C11D 7/3227* (2013.01); *C08J 9/143* (2013.01); *C08J 2203/166* (2013.01)

(58) Field of Classification Search
CPC ....... C07C 43/17; C07C 41/06; C11D 7/3227; C08J 9/143; C08J 2203/166
See application file for complete search history.

(56) References Cited

U.S. PATENT DOCUMENTS

| 2,799,712 | A | 7/1957 | Croix et al. |
| 5,589,557 | A | 12/1996 | Navarrini et al. |
| 2007/0203368 | A1 | 8/2007 | Tortelli et al. |
| 2016/0176791 | A1 | 6/2016 | Takahira |

FOREIGN PATENT DOCUMENTS

| JP | H07316235 A | 12/1995 |
| JP | H11147848 A | 6/1999 |
| JP | 2001151826 A | 6/2001 |
| JP | 2007169276 A | 7/2007 |
| JP | 2007238583 A | 9/2007 |
| JP | 2016160230 A | 9/2016 |
| WO | 2015033927 A1 | 3/2015 |

OTHER PUBLICATIONS

Murata et al. "Selective synthesis of fluorinated ethers by addition reaction of alcohols to fluorinated olefins in water", Green Chemistry, Feb. 2002, 4, pp. 60-63.*

Murata, Junji et al., "Selective synthesis of fluorinated ethers by addition reaction of alcohols to fluorinated olefins in water", Green Chemistry, vol. 4(No. 1), pp. 60-63 (Feb. 2002).

* cited by examiner

*Primary Examiner* — Rosalynd A Keys
(74) *Attorney, Agent, or Firm* — Browdy and Neimark, PLLC

(57) ABSTRACT

Provided is a novel compound that is expected to be used as a solvent, a cleaning agent, a blowing agent, an intermediate for a functional material, and so forth, as well as a production method therefor and uses thereof
As the novel compound, 1,2-dichoro-1-(2,2,2-trifluoroethoxy)ethylene is provided. This compound can be produced, for example, by allowing an addition reaction between 2,2,2-trifluoroethanol and trichloroethylene in the presence of a base.

9 Claims, No Drawings

1,2-DICHLORO-1-(2,2,2-TRIFLUOROETHOXY)ETHYLENE, PRODUCTION METHOD THEREFOR, AND USES THEREOF

TECHNICAL FIELD

The present invention relates to novel 1,2-dichoro-1-(2,2,2-trifluoroethoxy)ethylene (hereinafter, simply referred to as "DTE" in some cases) that is expected to be used as a solvent, a cleaning agent, a blowing agent, an intermediate for a functional material, and so forth, as well as a production method therefor and uses thereof.

BACKGROUND ART

There is abundant literature that discloses production methods for fluorine-containing olefins (Patent Literature (PTL) 1 to 5), but successful production of 1,2-dichoro-1-(2,2,2-trifluoroethoxy)ethylene of the present invention has not yet been reported.

CITATION LIST

Patent Literature

PTL 1: Japanese Unexamined Patent Application Publication No. 2016-160230
PTL 2: Re-publication of PCT International Publication No. 2015/033927
PTL 3: Japanese Unexamined Patent Application Publication No. 7-316235
PTL 4: Japanese Unexamined Patent Application Publication No. 2001-151826A
PTL 5: Japanese Unexamined Patent Application Publication No. 2007-169276

SUMMARY OF INVENTION

Technical Problem

An object of the present invention is to provide novel 1,2-dichoro-1-(2,2,2-trifluoroethoxy)ethylene, a production method therefor, and uses thereof.

Solution to Problem

The present invention provides the following.
[1] 1,2-Dichloro-1-(2,2,2-trifluoroethoxy)ethylene represented by the following formula (1).

[Formula 1]

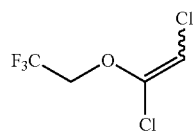

(1)

[2] 1,2-Dichloro-1-(2,2,2-trifluoroethoxy)ethylene according to [1] selected from the group consisting of trans-1,2-dichloro-1-(2,2,2-trifluoroethoxy)ethylene, cis-1,2-dichloro-1-(2,2,2-trifluoroethoxy)ethylene, and a combination thereof.

[3] A production method for 1,2-dichloro-1-(2,2,2-trifluoroethoxy)ethylene according to [1] or [2] comprising allowing an addition reaction between 2,2,2-trifluoroethanol and trichloroethylene in the presence of a base.

[4] The production method according to [3], where the addition reaction is carried out in the presence of an alkali metal hydroxide.

[5] The production method according to [3], where the addition reaction is carried out in the presence of sodium hydroxide and/or potassium hydroxide.

[6] A use of a composition containing 1,2-dichloro-1-(2,2,2-trifluoroethoxy)ethylene according to [1] or [2] as a solvent, a cleaning agent, or a blowing agent.

[7] A use of a composition containing 1,2-dichloro-1-(2,2,2-trifluoroethoxy)ethylene according to [1] or [2] as a cleaning agent for removing a flux or a process oil.

[8] A method of removing a contaminant from a substrate, comprising bringing the substrate into contact with a composition containing 1,2-dichloro-1-(2,2,2-trifluoroethoxy)ethylene according to [1] or [2].

[9] The method according to [8], where the contaminant is a flux or a process oil.

Advantageous Effects of Invention 1,2-Dichloro-1-(2,2,2-trifluoroethoxy)ethylene (DTE) of the present invention can be suitably employed for uses as a solvent, a cleaning agent, a blowing agent, an intermediate for a functional material, and so forth. Moreover, DTE of the present invention has a double bond within the molecule and thus readily decomposes in the atmosphere. For this reason, the global warming potential (GWP) and ozone depleting potential (ODP) are low.

Further, according to the production method of the present invention, it is possible to produce DTE of the present invention in an industrially advantageous manner and to control the isomer selectivity of DTE to be obtained as well.

DESCRIPTION OF EMBODIMENTS (Structure of the Compound of the Present Invention)
1,2-Dichloro-1-(2,2,2-trifluoroethoxy)ethylene, which is the compound of the present invention, has a chemical structure represented by the following formula (1).

[Formula 2]

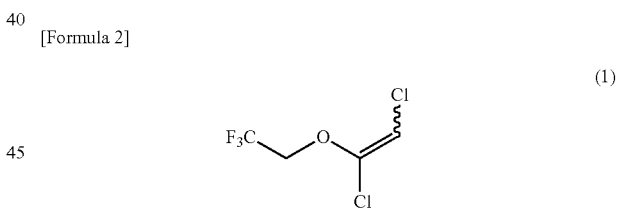

(1)

In the above formula (1), the chlorine atom bonded to the carbon-carbon double bond through a wavy line indicates that the chlorine atom is present at either the trans position or the cis position relative to the double bond. Accordingly, the compound of the present invention encompasses trans-1,2-dichloro-1-(2,2,2-trifluoroethoxy)ethylene, cis-1,2-dichloro-1-(2,2,2-trifluoroethoxy)ethylene, and a combination thereof. In accordance with the conventional notation, the symbol for hydrogen atoms is omitted in formula (1).

The compound of the present invention has a structure in which highly electronegative oxygen atom and chlorine atoms are directly bonded to the carbon-carbon double bond and forms a stable chemical structure as the entire molecule due to relatively widely dispersed electrons of the double bond. Meanwhile, due to the vinyl ether structure formed from a double bond and an oxygen atom, the compound of the present invention readily decomposes when released into the atmosphere. As just described, the compound of the present invention has functional groups as reaction sites, such as oxygen, chlorine, and a double bond, while being stable as the entire compound and thus acts as a reagent that reacts only under specific conditions. For this reason, the use as an intermediate for a functional material can be expected. Meanwhile, the compound of the present invention having two chlorine atoms exhibits excellent dissolution properties of organic substances, in particular, dissolution properties of oils. For this reason, the compound of the present invention is applicable to uses as a solvent, a cleaning agent, a blowing agent, and so forth.

(Production Method for the Compound of the Present Invention)

The compound of the present invention can be obtained, for example, by allowing an addition reaction between 2,2,2-trifluoroethanol and trichloroethylene in the presence of a base.

The reaction can be carried out under atmospheric pressure, and the reaction temperature is preferably set within the range of 50° C. to 100° C., which is slightly higher than normal temperature.

Examples of the base include alkali metal hydroxides, such as potassium hydroxide and sodium hydroxide. The concentration of the base is typically about 1 to 50 weight % based on 100 weight % for the reaction solution as a whole. In particular, when an aqueous solution of an alkali metal hydroxide is used, the base concentration is preferably 5 to 50 weight %, more preferably 8 to 40 weight %, further preferably 5 to 35 weight %, and most preferably 5 to 15 weight % based on 100 weight % for the reaction solution as a whole.

A solvent may be any solvent provided that the base can be dissolved, and not just water, but water-soluble organic solvents, polar aprotic organic solvents, and further, mixed solvents thereof may also be used. Examples of the water-soluble organic solvents include lower alcohols, such as methanol, ethanol, propanol, and butanol; and ether solvents, such as glyme and diglyme (Dig). Examples of the polar aprotic organic solvents include dimethylformamide (DMF), acetonitrile, dimethyl sulfoxide (DMSO), and hexamethylphosphoramide (HMPA). In view of availability and costs, water or a mixed solvent with water is preferably used.

When the reaction is carried out in a two-phase system of an aqueous phase and an organic phase, the presence of a phase transfer catalyst in the reaction system is desirable from a viewpoint of enhancing the reaction efficiency. The amount of the phase transfer catalyst is preferably 0.1 to 10 mol % and more preferably 0.5 to 5 mol % based on 100 mol % for the amount of 2,2,2-trifluoroethanol (TFEOH). Examples of the phase transfer catalyst include quaternary ammonium salts, such as tetrabutylammonium bromide (TBAB), trioctylmethylammonium salts, and benzyldimethyloctadecylammonium salts; and crown ethers.

(Uses of the Compound of the Present Invention)

As in the foregoing, the compound of the present invention having two chlorine atoms exhibits excellent dissolution properties of organic substances, in particular, dissolution properties of oils. By exploiting these properties, the compound of the present invention is applicable to the following uses.

(1) Uses as Solvents and Cleaning Agents

The compound of the present invention can be mixed, at any suitable ratio, with organic solvents including, for example, ketones, such as acetone and acetophenone; nitriles, such as acetonitrile and propionitrile; ethers, such as diisopropyl ether, tert-butyl methyl ether, tetrahydrofuran, diglyme, and 1,4-dioxane; sulfoxides, such as dimethyl sulfoxide and sulfolane; amides, such as dimethylformamide, dimethylacetamide, and N-methylpyrrolidone; hydrocarbons, such as hexane, heptane, cyclohexane, benzene, and toluene; and alcohols, such as methanol, ethanol, and isopropanol. Accordingly, the compound of the present invention can be widely used as mixed solvents. Moreover, the compound of the present invention exhibits particularly excellent dissolution properties of oils and thus can be suitably used as a cleaning agent.

The boiling point of the compound of the present invention is 35° C./35 hPa (corresponding to about 120° C./1,013 hPa). Accordingly, the compound of the present invention has low volatility in a common working environment and thus contributes to improvements in the working environment.

(2) Uses as Blowing Agents

By exploiting the dissolution properties of organic substances, the compound of the present invention can be used for preparing foamable compositions of thermosetting resins, such as polyurethanes, or thermoplastic resins, such as polystyrene, polyethylene, and polypropylene.

EXAMPLES

Hereinafter, the present invention will be described by means of concrete examples. However, the scope of the present invention is by no means limited to the following examples.

Example 1

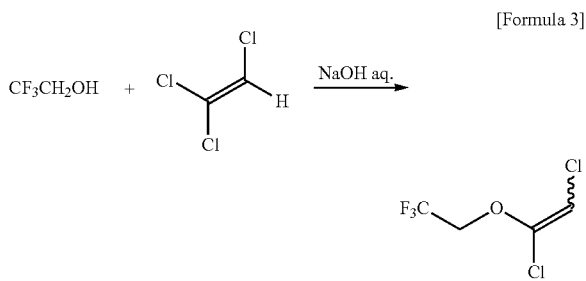

[Formula 3]

In the above reaction formula, NaOH aq. indicates an aqueous solution of sodium hydroxide.

To a 1 L three-necked flask equipped with a condenser, 72 g (1.8 mol) of NaOH and 504 g of water were fed in this order and 90.0 g (900 mmol) of 2,2,2-trifluoroethanol (TFEOH) was added over 1.5 hours. Subsequently, 124.2 g (944 mmol) of trichloroethylene (TCE) was added and finally, 3.46 g (10.7 mmol) of tetrabutylammonium bromide (TBAB) was added as a phase transfer catalyst. The resulting reaction solution was heated to 70° C., reacted for 20 hours, and then brought back to room temperature. The resulting organic layer was separated and purified by distillation to yield 150 g of 1,2-dichloro-1-(2,2,2-trifluoroethoxy)ethylene, which is the compound of the present invention (84% yield).

The spectral data used for identifying the obtained compound will be shown below. The following NMR and GC analysis results revealed a single compound.

$^1$H NMR (CDCl$_3$): 4.31 (q, J=8 Hz, 2H), 5.64 (s, 1H)

$^{19}$F NMR (CDCl$_3$): −74.1 (t, J=8 Hz, 3F)

$^{13}$C NMR (CDCl$_3$): 66.7 (q, CF$_3$CH$_2$CCl=CClH), 101.0 (d, CF$_3$CH$_2$CCl=CClH), 122.5 (q, CF$_3$CH$_2$CCl=CClH), 141.9 (s, CF$_3$CH$_2$CCl=CClH)

GC: CF$_3$CH$_2$OH at 2.1 min, TCE at 3.7 min, the compound of the present invention at 5.1 min, diglyme at 9.1 min GC-MS: 7.7 min, molecular weight 194

Boiling point: 35° C./35 hPa (corresponding to about 120° C./1,013 hPa)

Examples 2 to 14

The compound of the present invention was prepared in the same manner as Example 1 except for changing the reaction conditions as shown in the following Table.

TABLE 1

| Ex. | TFEOH g | TCE g | Base | Solvent g (g) | TBAB mol % | Temperature °C. | Time hr | Conversion % | Selectivity % | Yield % (isolated yield) |
|---|---|---|---|---|---|---|---|---|---|---|
| Ex. 1 | 90 | 124.2 | NaOH | 72 H$_2$O (504) | 1.2 | 70 | 20 | 99 | 95 | 94 (84) |
| Ex. 2 | 1 | 1.4 | KOH | 1.1 DMF (5) | — | 65 | 2 | 98 | 80 | 78 |
| Ex. 3 | 15 | 20 | KOH | 16.8 DMF (47) | — | 65 | 2 | 99 | 75 | 74 |
| Ex. 4 | 5 | 6.7 | KOH | 5.6 Dig/H$_2$O (14/20) | 1.2 | 65 | 14 | 98 | 95 | 93 |
| Ex. 5 | 30 | 41.4 | KOH | 33 Dig/H$_2$O (84/60) | 1.2 | 65 | 12 | 98 | 93 | 92 |
| Ex. 6 | 90 | 124 | KOH | 101 Dig/H$_2$O (197/180) | 1.2 | 65 | 14 | 99 | 95 | 91 |
| Ex. 7 | 5 | 6.7 | KOH | 5.6 H$_2$O (6) | 1.2 | 65 | 14 | 99 | 81 | 80 |
| Ex. 8 | 5 | 6.7 | NaOH | 4 H$_2$O (16) | 1.2 | 65 | 60 | 99 | 90 | 89 |
| Ex. 9 | 5 | 6.7 | NaOH | 4 H$_2$O (28) | 1.2 | 65 | 20 | 99 | 94 | 93 |
| Ex. 10 | 5 | 6.7 | NaOH | 4 H$_2$O (36) | 1.2 | 65 | 20 | 91 | 95 | 86 |
| Ex. 11 | 5 | 6.7 | NaOH | 4 H$_2$O (22.6) | 1.2 | 65 | 20 | 91 | 94 | 85 |
| Ex. 12 | 5 | 6.7 | NaOH | 4 H$_2$O (28) | 1.2 | 65 | 20 | 98 | 94 | 92 |
| Ex. 13 | 270 | 354 | NaOH | 214 H$_2$O (1503) | 1.2 | 65 | 20 | 100 | 95 | 95 |

In the above Table, "TFEOH" represents 2,2,2-trifluoroethanol, "TCE" represents trichloroethylene, "TBAB" represents tetrabutylammonium bromide, and "Dig/H$_2$O (14/20)" indicates a mixed solvent of 14 g of diglyme and 20 g of water. The amount of "TBAB" is a value based on 100 mol % for the amount of TFEOH. KOH was mixed with DMF solvent after ground into powder.
The yield is a GC yield, and an isolated yield is shown within the parentheses for Example 1.

[Cleaning Capability Assessment Test]

The solubility (cleaning capability) of each contaminant in the compound of the present invention is shown in the following Table. In the Table, the numerical values represent the number of grams of the respective contaminants dissolved in 100 g of a solvent. The term "miscible" means that 100 g of a contaminant dissolved in 100 g of a solvent.

[Formula 1]

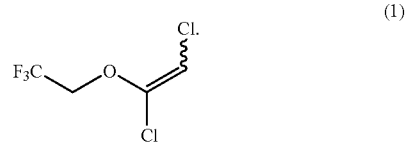

(1)

TABLE 2

| Contaminant | | | Compound of present invention | | ZEORORA HTA[*1] | | AE-3000 | AK-225[*1] | 1233Z |
|---|---|---|---|---|---|---|---|---|---|
| Product name | Manufacturer | Classification | 25° C. | 40° C. | 25° C. | 40° C. | 25° C. | 25° C. | 25° C. |
| Abietic acid | Tokyo Chemical Industry Co., Ltd. | Flux component | 6.3 | 6.6 | 0.3 | — | 0.1 | 1.1 | 0.3 |
| G-6050 | Nihon Kohsakuya Co., Ltd. | Blanking oil | Miscible | Miscible | 3.5 | 5.4 | 2.2 | Miscible | Miscible |
| G-6040 | Nihon Kohsakuya Co., Ltd. | Blanking oil | Miscible | Miscible | 2.9 | 3.6 | 0.8 | Miscible | Miscible |
| C-126 | Nihon Kohsakuya Co., Ltd. | Cutting Fluid | Miscible | Miscible | Miscible | Miscible | Miscible | Miscible | Miscible |
| Castor oil | Kanto Chemical Co., Inc. | Vegetable oil | Miscible | Miscible | 0.6 | 1.0 | 0.6 | Miscible | Miscible |
| Olive oil | Kanto Chemical Co., Inc. | Vegetable oil | Miscible | Miscible | 0.2 | 0.7 | 0.6 | Miscible | Miscible |

[*1]Reference material, Development of Cleaning Technology, CMC Publishing Co., Ltd.
*2: All of ZEORORA ® HTA, AE-3000, and AK-225 are trade names for cleaning agents.
*3: 1233z is an abbreviation for cis-1-chloro-3,3,3-trifluoropropene.

As shown in the above Table, the compound of the present invention had unexpectedly favorable assessment results of not only being "miscible" with all the process oils but also exhibiting better dissolution properties of a flux (abietic acid), whose removal is generally considered difficult, than the existing cleaning agents.

The invention claimed is:

1. 1,2-Dichloro-1-(2,2,2-trifluoroethoxy)ethylene represented by the following formula (1)

2. 1,2-Dichloro-1-(2,2,2-trifluoroethoxy)ethylene according to claim 1 selected from the group consisting of trans-1,2-dichloro-1-(2,2,2-trifluoroethoxy)ethylene, cis-1,2-dichloro-1-(2,2,2-trifluoroethoxy)ethylene, and a combination thereof.

3. A production method for 1,2-dichloro-1-(2,2,2-trifluoroethoxy)ethylene according to claim 1 comprising allowing an addition reaction between 2,2,2-trifluoroethanol and trichloroethylene in the presence of a base.

4. The production method according to claim 3, wherein the addition reaction is carried out in the presence of an alkali metal hydroxide.

5. The production method according to claim 3, wherein the addition reaction is carried out in the presence of sodium hydroxide and/or potassium hydroxide.

6. A solvent, cleaning agent or blowing agent, comprising a composition containing 1,2-dichloro-1-(2,2,2-trifluoroethoxy)ethylene according to claim 1.

7. A cleaning agent for removing a flux or a process oil, comprising a composition containing 1,2-dichloro-1-(2,2,2-trifluoroethoxy)ethylene according to claim 1.

8. A method of removing a contaminant from a substrate, comprising bringing the substrate into contact with a composition containing 1,2-dichloro-1-(2,2,2-trifluoroethoxy)ethylene according to claim 1.

9. The method according to claim 8, wherein the contaminant is a flux or a process oil.

* * * * *